(12) United States Patent
Donovan et al.

(10) Patent No.: US 12,400,186 B2
(45) Date of Patent: Aug. 26, 2025

(54) PERSONALIZED MEDICAL ADJUDICATION AND TREATMENT SYSTEM

(71) Applicant: MEDIMPACT HEALTHCARE SYSTEMS, INC., San Diego, CA (US)

(72) Inventors: Matthew Christopher Jon Donovan, Tempe, AZ (US); Richard G. Jimenez, San Diego, CA (US); Karen Geary, Newton, PA (US); Steven Secker, San Diego, CA (US)

(73) Assignee: MEDIMPACT HEALTHCARE SYSTEMS, INC., San Diego, CA (US)

( * ) Notice: Subject to any disclaimer, the term of this patent is extended or adjusted under 35 U.S.C. 154(b) by 775 days.

(21) Appl. No.: 17/187,215

(22) Filed: Feb. 26, 2021

(65) Prior Publication Data

US 2021/0264363 A1 Aug. 26, 2021

Related U.S. Application Data

(60) Provisional application No. 62/982,021, filed on Feb. 26, 2020.

(51) Int. Cl.
*G06Q 10/10* (2023.01)
*G16H 10/60* (2018.01)
*G16H 20/10* (2018.01)

(52) U.S. Cl.
CPC .............. *G06Q 10/10* (2013.01); *G16H 10/60* (2018.01); *G16H 20/10* (2018.01)

(58) Field of Classification Search
CPC ........ G06Q 10/10; G16H 10/60; G16H 20/10; G16H 40/20; G16H 50/70
See application file for complete search history.

(56) References Cited

U.S. PATENT DOCUMENTS

| 11,043,293 B1* | 6/2021 | Salzbrenner | G16H 10/60 |
| 2009/0210253 A1* | 8/2009 | Ash | G16H 50/20 600/595 |
| 2010/0063835 A1* | 3/2010 | Kenedy | G16B 50/00 705/2 |
| 2018/0082030 A1* | 3/2018 | Allen | G16H 70/40 |
| 2019/0164637 A1 | 5/2019 | Coleman et al. | |
| 2020/0365280 A1* | 11/2020 | Todd | G16H 40/20 |

* cited by examiner

*Primary Examiner* — Rachelle L Reichert
(74) *Attorney, Agent, or Firm* — Mintz Levin Cohn Ferris Glovsky and Popeo, P.C.

(57) ABSTRACT

Computer implemented systems and methods for adjudication of treatments and prescriptions for a patient are provided. The method may comprise receiving a request to approve a medical request for administering a treatment to a patient; accessing a database of genetic information to determine genetic information of the patient; comparing the genetic information of the patient against a database of pharmacogenetic information in view of the medical request; and providing a response to the medical request, the response including one or more of administering the treatment to the patient, or offering an alternate treatment for the patient.

16 Claims, 5 Drawing Sheets

| ENTERED | MEMBER_NO | FAMILY POSITION | DRUG_CODE | SEVERITY_LEVEL | PHYSICIAN_RESPONSE | POS_ACTION | drug_name |
|---|---|---|---|---|---|---|---|
| 8/9/2019 | 123ABCDEFG | 1 | 17539 | RED | EXPLICIT DISCONTINUE | DENY | Clopidogrel |
| 8/9/2019 | 123ABCDEFG | 1 | 6312 | RED | EXPLICIT CONTINUE | APPROVE | Simvastatin |
| 8/9/2019 | 123ABCDEFG | 1 | 2064 | YELLOW | NEW TO THERAPY | APPROVE | Amphetamine |
| 8/9/2019 | 123ABCDEFG | 1 | 13449 | YELLOW | NEW TO THERAPY | APPROVE | Amphetamine |
| 8/9/2019 | 123ABCDEFG | 1 | 42716 | YELLOW | NEW TO THERAPY | APPROVE | Amphetamine |
| 8/9/2019 | 123ABCDEFG | 1 | 12404 | YELLOW | EXPLICIT CONTINUE | APPROVE | Atorvastatin |
| 8/9/2019 | 123ABCDEFG | 1 | 25951 | YELLOW | EXPLICIT CONTINUE | APPROVE | Atorvastatin |
| 8/9/2019 | 123ABCDEFG | 1 | 41264 | YELLOW | NEW TO THERAPY | APPROVE | Beleodaq |
| 8/9/2019 | 123ABCDEFG | 1 | 1653 | YELLOW | NO RESPONSE | APPROVE | Bupropion |
| 8/9/2019 | 123ABCDEFG | 1 | 36156 | YELLOW | NO RESPONSE | APPROVE | Bupropion |
| 8/9/2019 | 123ABCDEFG | 1 | 41389 | YELLOW | NO RESPONSE | APPROVE | Bupropion |
| 8/9/2019 | 123ABCDEFG | 1 | 6536 | YELLOW | NEW TO THERAPY | APPROVE | Clobazam |
| 8/9/2019 | 123ABCDEFG | 1 | 22987 | YELLOW | NEW TO THERAPY | APPROVE | Dexmethylphe |
| 8/9/2019 | 123ABCDEFG | 1 | 2065 | YELLOW | NEW TO THERAPY | APPROVE | Dextroamphet |
| 8/9/2019 | 123ABCDEFG | 1 | 1656 | GREEN | NO GENE VARIANT | APPROVE | Amitriptyline |
| 8/9/2019 | 123ABCDEFG | 1 | 13819 | GREEN | NO GENE VARIANT | APPROVE | Amitriptyline |
| 8/9/2019 | 123ABCDEFG | 1 | 1648 | GREEN | NO GENE VARIANT | APPROVE | Amoxapine |
| 8/9/2019 | 123ABCDEFG | 1 | 16576 | GREEN | NO GENE VARIANT | APPROVE | Anzemet |

PERSONALIZED MEDICAL ADJUDICATION AND TREATMENT SYSTEM

CROSS-REFERENCE TO RELATED APPLICATIONS

This application claims priority to and the benefit of the earlier filing date of U.S. Provisional Patent Application Ser. No. 62/982,021 filed on Feb. 26, 2020, the content of which is hereby incorporated by reference herein in its entirety.

TECHNICAL FIELD

The disclosed subject matter generally relates to personalized medicine and, more particularly, to computer-implanted methods to facilitate medical adjudication as compatible with a patient's profile distinguished by genetics, diagnosis, or other personal traits.

BACKGROUND

When a patient is diagnosed or treated by a medical provider, the medical provider may not know or may miss certain patient genetic attributes or conditions. In some cases, the medical provider may not be aware of adverse effects that a selected medical treatment or medication may have on a patient with certain diagnosis or genetic attributes or not be up-to-date about the latest evidence regarding drug side effects or drug related genetic attributes. As a result, the medical provider may order medication that may either jeopardize the patient's health or fail to most effectively treat or cure the patient. In such cases, the medical provider may be scrutinized, especially if it is determined that there was an error in the diagnosis process.

Advances in the medical and diagnostics technology can help streamline medical adjudication and reduce risks and costs to patients, medical providers and healthcare insurers. For example, pharmaceutical contraindication systems are currently available that can determine whether a certain prescribed medicine to a patient may have an unintended adverse effect (e.g., due to counter interaction with another medicine that the patient is then taking). Often, such systems are limited in scope to data related to interactions between certain medications and are generally only used at the point of sale (e.g., at the pharmacy) and not by a physician at the point of care or during diagnosis. Also, no system is currently provided that allows for patient self-advocacy based on personal information such as genetic data.

Further, the currently available systems do not take a patient's genetic profile or different aspects of personalized data into consideration. Genetic data, specifically in the form of interpreted findings, can help determine whether a prescribed medication or medical procedure will provide clinical efficacy or, on the opposite end, whether the medication may increase the risk of known adverse reactions in patients. Other personalized data such as diagnosis or patient specific risk profiles can help define prescribed medications that should be avoided. Accordingly, systems and methods are needed that can overcome the above shortcomings by improving on time and real-time access to relevant information to support advancements in medical adjudication, patient care and treatment outcomes.

SUMMARY

For purposes of summarizing, certain aspects, advantages, and novel features have been described herein. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested herein.

In accordance with some implementations of the disclosed subject matter, computer implemented systems and methods for adjudication of treatments and prescriptions for a patient are provided. The method may comprise receiving a request to approve a medical request for administering a treatment to a patient, accessing a database of clinical information to determine personal clinical information of the patient, comparing the information of the patient against a database of standardized, population based information in view of the medical request, and providing a response to the medical request, the response including one or more of administering the treatment to the patient, or offering an alternate treatment for the patient.

In one or more embodiments, the request is processed by a claim processing system with access to a database of claims history for the patient. Personal information such as genetic information of the patient may be stored in a repository of genetic information. The genetic information of the patient may be provided by a third party vendor. The genetic information of the patient may include information about a DNA mutation with, for example, a single nucleotide polymorphisms (SNP). The SNP may be a missense mutation, a nonsense mutation. In some embodiments, the DNA mutation may include a deletion, an insertion, a duplication, a frameshift mutation or a repeat expansion.

To further illustrate an instance of the personalized nature of the subject matter, the database of pharmacogenetic information may include comparative information indicating the treatment may be ineffective or cause an adverse reaction based on the genetic information of the patient. The database of pharmacogenetic information may include comparative information indicating the treatment may be suboptimal based on the genetic information of the patient. The database of pharmacogenetic information may be linked to a database of alternative solutions for the treatment requested.

In certain embodiments the response may include at least one or more of a warning, an alternative treatment or drug solution, a denial of the treatment request, an approval of the treatment request, or an alternative dosage associated with a prescribed medication as a part of the treatment request. In at least one aspect, the response comprises suggesting administration of a genetic test to the patient.

Depending on implementation, the user of the claim processing system may be a pharmacist, a patient, a prescribing physician, a physician assistant, or an insurance representative. The processing system may be continuously updated with information from one or more databases. The databases including diagnosis, pharmacogenetic information and genetic information may be also updated by adding new data based on domestic or international genetic research.

Implementations of the current subject matter may include, without limitation, systems and methods consistent with the above methodology and processes, including one or more features and articles that comprise a tangibly embodied machine or computer-readable medium operable to cause one or more machines (e.g., computers, processors, etc.) to result in operations disclosed herein, by way of, for example, logic code or one or more computing programs that cause one or more processors to perform one or more of the disclosed operations or functionalities. The machines may exchange data, commands or other instructions via one or more connections, including but not limited to a connection over a network.

The details of one or more variations of the subject matter described herein are set forth in the accompanying drawings and the description below. Other features and advantages of the subject matter described herein will be apparent from the description and drawings, and from the claims. The disclosed subject matter is not, however, limited to any particular embodiment disclosed.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations as provided below.

The figures may not be to scale in absolute or comparative terms and are intended to be exemplary. The relative placement of features and elements may have been modified for the purpose of illustrative clarity. Where practical, the same or similar reference numbers denote the same or similar or equivalent structures, features, aspects, or elements, in accordance with one or more embodiments.

DETAILED DESCRIPTION OF EXAMPLE IMPLEMENTATIONS

In the following, numerous specific details are set forth to provide a thorough description of various embodiments. Certain embodiments may be practiced without these specific details or with some variations in detail. In some instances, certain features are described in less detail so as not to obscure other aspects. The level of detail associated with each of the elements or features should not be construed to qualify the novelty or importance of one feature over the others.

In accordance with one or more embodiments, computer-implemented systems and methods are provided for processing a request submitted by a medical provider. The request may be submitted in relation to a medical treatment ordered for a patient, for example. The medical treatment may be a prescription for a medication, drug therapy or other type of medical procedure, such as diagnostic test for patient evaluation. The medical request may be processed by a claim adjudication system, based on information accessible via one or more databases. Without limitation, a database may include genetic or pharmacogenetic information, diagnosis, laboratory values, risk factors or historical references to prior health care services.

In an illustrative genetic example embodiment, the one or more databases may include genetic information about a particular patient or groups of patients with similar or diverse genetic backgrounds. The genetic data about a patient may include information defining one or more of structurally normal DNA, structural mutations, deletions, insertions, duplications, frameshift mutations, or repeat expansions, for example.

The one or more databases may also include pharmacogenetic or other personalized information about how administration of certain medical treatments or therapies may affect a population of patients with similar characteristics and attributes, or a particular patient individually. The population may include patients that fit the same or similar profile as a particular patient (e.g., target patient or subject patient). Accordingly, a submitted request for treatment of a patient and the patient's genetic information may be compared and analyzed against the pharmacogenetic information about how a patient with certain genetic characteristics may respond to the ordered medical treatment in the submitted request.

Pharmacogenetics is the study of how individual patients respond differently to drug therapy or certain medications based upon their particular genetic makeup or genes. The term pharmacogenetics data, as used herein, refers to any kind of data that has been scientifically or experimentally collected or developed and, without limitation, can be used to identify how an individual patient or group of patients, with certain genetic attributes, may respond to any type of medical treatment, pharmaceutical drugs, medical procedure, prescription, medication or psychiatric therapy, or the like.

Diet, overall health, and environment also influence the outcome of medical treatment or medication therapy. However, the genetic makeup of the subject patient under therapy is the most deterministic factor in the success or failure of certain types of treatment. For other types of treatment, concurrent patient diagnosis become the most deterministic factor. To provide for patient comfort, treatment efficacy and costs saving, it would be desirable to determine the chances of treatment success based on certain factors, including a patient's genetic background and/or co-morbidities, at the early stages of diagnosis or treatment and ideally prior to the medication being administered or the therapy or medical treatment being initiated.

For example, antidepressant medications are largely metabolized by enzymes created based on DNA in the CYP2C19 gene. Studies have shown that in nearly 19% of the population, this DNA generates higher levels of enzymes than found in the general population on average. Consequently, these antidepressants are eliminated out of the body faster in those patients that generate higher levels of the enzyme. Knowing the genetic disposition of individual patients can allow for a higher dose than standard to be prescribed for patients in which the DNA generates higher levels of the enzymes. In this manner, a higher first dose may be prescribed at the outset without delay, as it is known that the lower standard dose would fail to perform as needed, if prescribed.

Advantageously, in accordance with one or more embodiments, pharmacogenetic data may be utilized to determine patient compatibility with drug selection, drug administration, or drug therapy. In some implementations, additional information about an individual's diet, health and surroundings may also be analyzed to determine the respective influences on medication responses in view of the patient's genetic makeup. For example, pharmacogenetic data may be used to determine correlations between genetic variations (e.g., DNA mutations) and drug efficacy or safety for an individual patient or group of patients. Ordered therapy or corresponding doses may also be determined or adjusted based on such data.

For example, ibuprofen is commonly used to address muscle aches and pain. Studies have shown that certain individuals with a genetic variant in gene CYP2C9 are poor metabolizer and therefore have a higher risk of toxicity and potential for side effects such as gastric bleeding. Accordingly, in certain embodiments, a personalized prescription adjudication system may be implemented that provides an alert, if an individual patient carrying the gene variant CYP2C9 is prescribed ibuprofen. The adjudication system may further provide an alternative medication to ibuprofen that help with muscle aches and pain, but does not cause an adverse reaction for the particular patient.

As such, in certain embodiments, genetic information of a patient may be accessed and analyzed in view of available pharmacogenetic data. In doing so, matching the patient's genetic information with known genetic variation data in a pharmacogenetic database may provide helpful and important insights and conclusions about the compatibility of a requested medical treatment for that patient according to the patient's pertinent genetic profile. As provided in further detail herein, based on the compatibility results, it may be appropriate to deny a prescribed treatment, provide alternative treatments (e.g., drug selections), or suggest altered dosages or combination therapies.

For example, clopidogrel is frequently prescribed following the placement of a stent in a cardiac vessel to prevent the possible formulation of blood clots on the stent. Such clots, if present, may break free and cause a stroke or heart attack. Clopidogrel is prescribed to prevent such clot formations. However, genetics may cause clopidogrel to be ineffective, causing the patient to continue to be at risk for blood clot formation and potential strokes and heart attacks. Personalized genetic information, in accordance with one or more embodiments, may be utilized to alert the prescriber with an alert if clopidogrel is prescribed to a patient with an adverse genetic disposition. Stopping the use or administering of clopidogrel in this example would prevent morbidity and mortality.

In the following, certain embodiments are disclosed by way of example as associated with validating a request for drug therapy to be administrated to a particular patient based on pharmacogenetic data. It is noteworthy, however, that various embodiments may be utilized for validating other types of medical requests and using data that may or may not include pharmacogenetic data. For example, in addition to or instead of submitting a request for validating genetically aligned prescribing or administering a certain drug therapy, the request may be for validation of drug use in select conditions (e.g., chronic kidney disease) or for prescribing a diagnostic test or procedure that may already be on record, or alerting prescribing concerns based upon social risk factors such as adequate access to care monitoring, etc.

Figure 1:
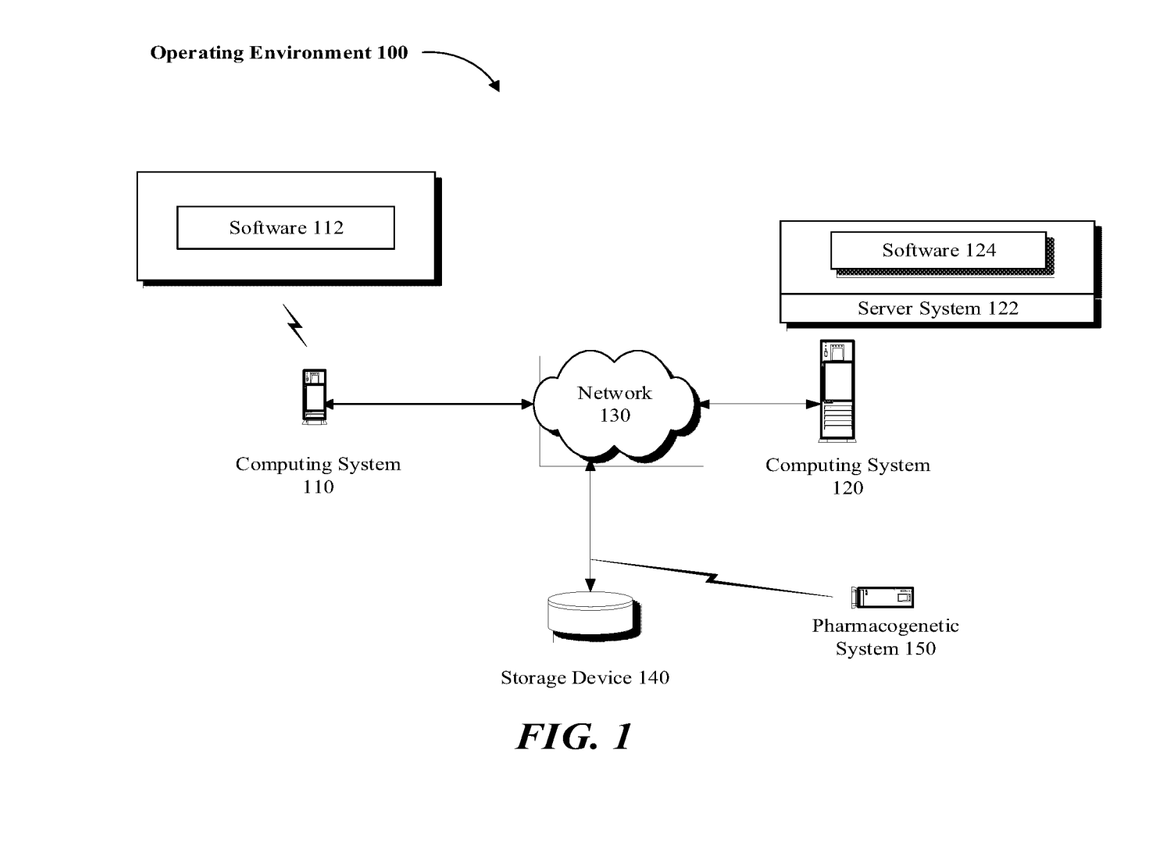
FIG. 1 illustrates an example operating environment, in accordance with one or more embodiments, wherein a prescription or treatment request for a patient may be submitted.

Referring to FIG. 1, an example claim adjudication system in operating environment 100 is illustrated. As shown, a computing system 110 may be utilized by a user (e.g., a medical provider) to interact with software 112 being executed on computing system 110. Computing system 110 may be utilized to process or facilitate the processing of a medical order or a treatment for an individual (e.g., a patient). The computing system 110 may be a general-purpose computer, a handheld mobile device (e.g., a smart phone), a tablet (e.g., an Apple iPad®), or other communication capable computing device. Software 112 may be a web browser, a dedicated app or other type of software application running either fully or partially on computing system 110.

Computing system 110 may communicate over a network 130 to initiate a medication claim through computing system 120. Genetic or pharmacogenetic data may be stored on one or more storage devices 140 and may be access by computing systems 110 or 120. The computing system 120 may be configured for claim adjudication (e.g., processing a medical order or drug prescription) and for accessing genetic or pharmacogenetic data stored on one or more storage devices 140. Depending on implementation, storage device 140 may be local to, remote to, or embedded in one or more of computing systems 110 or 120. A server system 122 may be configured on computing system 120 to service one or more requests submitted by computing system 110 or software 112 (e.g., collectively client systems) via network 130. Network 130 may be implemented over a local or wide area network (e.g., the Internet).

Computing system 120 and server system 122 may be implemented over a centralized or distributed (e.g., cloud-based) computing environment as dedicated resources or may be configured as virtual machines that define shared processing or storage resources. Execution, implementation or instantiation of software 124, or the related features and components (e.g., software objects), over server system 122 may also define a special purpose machine that provides remotely situated client systems, such as computing system 110 or software 112, with access to a variety of medical claim adjudication services for determining or analyzing the compatibility of a prescribed drug or medical procedure or test with a particular patient or individual.

In accordance with one or more aspects, the adjudication system of FIG. 1 and the related services provided by the special purpose machine or software 124 may include providing a user, using computing system 110 or software 112, with options for submitting, reviewing, verifying or facilitating the ordering of a medical request or claim. As provided herein, the medical request or claim may include any or one or more of a drug prescription, a medical procedure, an order for medication therapy, a test or any other medical, pharmaceutical, psychiatric or therapeutic-related order or request.

Continuing to refer to FIG. 1, network 130 in conjunction with server system 122 may be utilized to coordinate the communication and analysis of the submitted order or request, in view of relevant medical or genetic information and patient history, as provided in further detail herein. For example, a pharmacogenetic information provider or database (not shown) may be coupled to computing system 120 (e.g., via a network 130) to provide access to genetic or pharmacogenetic information about one or more individuals. The database may be deployed over storage device 140 and the genetic information may be provided or accessed at the time a medical order or medication treatment is submitted to server system 122 for processing.

Access to the services of server system 122 may be provided to a medical provider at the time of care, either in real-time or near real-time, for example. In certain scenarios, one or more medical providers, technicians or users, such as a pharmacist, a doctor, or a physician's assistant may access the services for adjudication of one or more claims. Network 130 may, thus, include a claims processing system in which a healthcare insurer or benefits manager adjudicates the related claims for payment. For example, after a medical claim is submitted, a benefits manager or insurance company may determine the financial responsibility for the payment and decide to approve the claim in full, deny the claim, or to reduce the amount payable to the provider.

Operating environment 100 may also include a pharmacogenetic information system, which can provide pharmacogenetic information to be stored or added to a pharmacogenetic database implemented over storage device 140. Importantly, pharmacogenetic data can be periodically updated to reflect the latest results from publicly available studies and sources. For example, the pharmacogenetic data may include results from clinical studies and professional sources of genetic data. Pharmacogenetic data, medical diagnosis and any other information that may be helpful in determining contraindications for a specific or group of patients may be stored on storage device 140. Storage device 140 or another storage system may store information about the patients including, without limitation, patient identity, medical history, claim history, and genetic data including any genetic variation in a secure manner.

Figure 2:
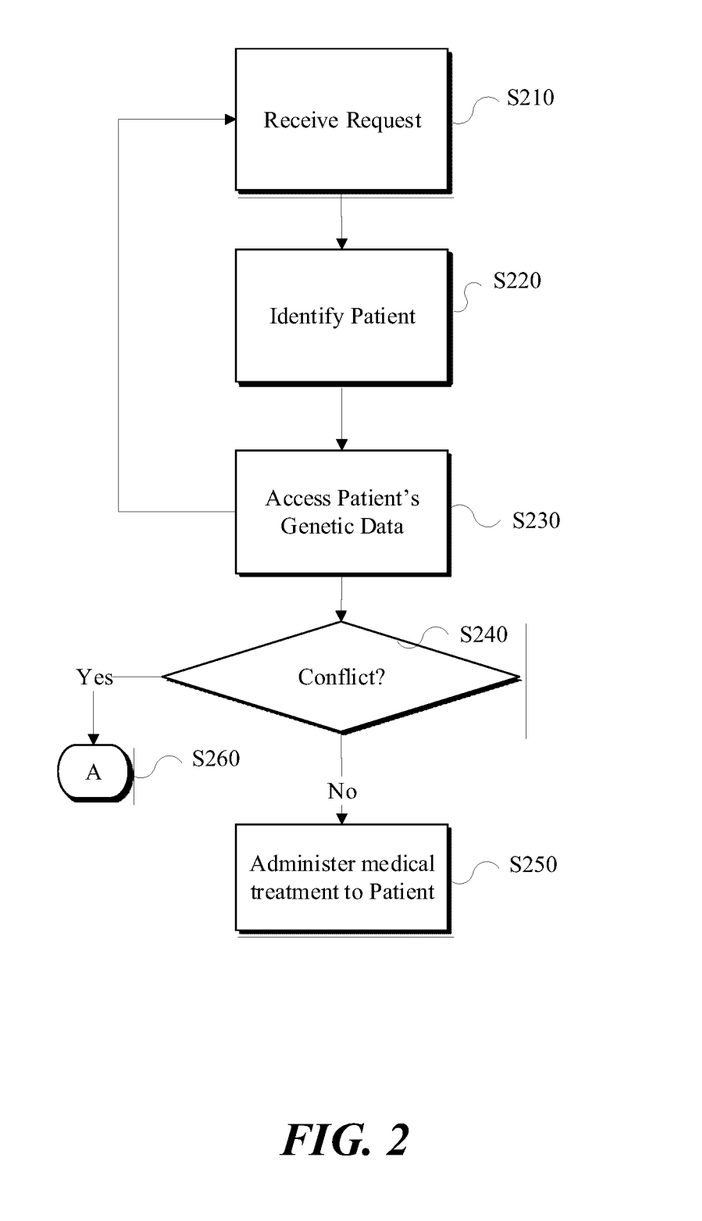
FIG. 2 is an example flow diagram of a method of processing a request for a prescription or treatment, in accordance with one embodiment.

Referring to FIGS. 1 and 2, a computer-implemented method for processing a medical request to fulfill a medical order or medication treatment, using the operating environment 100 of FIG. 1, is provided. A medical request including a medical order (e.g., a medication treatment, pharmaceutical prescription, medical procedure, etc.) may be entered into the system by way of a user (e.g., a physician, a physician's assistant, a pharmacist, etc.) interacting with computing system 110. The request is thus received by computing system 110 (S210). The received request may be processed by software 112 running on computing system 110 and thereafter transmitted to computing system 120 over network 130. The submitted request may include identifying information about a subject patient and the specifics of the medical order for the subject patient.

Server system 122 may receive the medical request transmitted to computing system 120 and process the request against data stored or staged on storage device 140 to determine the identity of the patient (S220). If the patient is not identified by searching the records in storage device 140, then software 124 may communicate with one or more other resources (e.g., a claims adjudication system) to obtain information that may help identify the subject patient for whom the medical request is being processed. If the patient cannot be identified, the medical request may be rejected or a response may be generated and forwarded to computing system 110 to notify the user that the patient cannot be identified. The user may be provided with an opportunity to enter the medical request again, possibly, along with patient information or any missing information.

Software 124, depending on implementation, may be utilized in an example medical claim adjudication environment to accesses patient genetic information from a genetic database (S230). The genetic database may be stored on storage device 140 or other data storage system, either locally or remotely accessible to computing system 120. As noted herein, pertinent patient information such as genetic variations, diagnosis history, claims history, prognosis history, allergies, pharmaceutical contraindications and any other medical and diagnostic information about the subject patient may be stored in and accessed via the genetic database. Such information may also be available and provided through one or more third party resources.

In certain implementations, if genetic information for the patient is not available or accessible, then software 124 may generate a response to computing system 110, indicating that the subject patient should undergo genetic testing. The medical provider who submitted the request may be also advised that the medical request is to be resubmitted, possibly with the requisite test results or when the test results are independently uploaded to the system. In some aspects, the approval of the submitted medical request may be conditioned upon the patient undergoing the genetic testing and the submission of the complete, or at least partial, genetic results. As such, a medical request or a related claim submitted for a patient may be denied or delayed until the genetic information for the patient is made available.

Continuing to refer to FIGS. 1 and 2, in one or more embodiments, pharmacogenetic information about the subject patient may be added to the genetic database by way of a pharmacogenetic system 150, for example. The pharmacogenetic system 150 may be a software as a service (SaaS) provider (e.g., Translational Software) with technology to support translating genetic data into actionable data based on clinical guidance of one or more expert groups with full integration capabilities to support interoperability for various application programing interfaces (APIs) and standards (e.g., FHIR®, LOINC, and HL7) in a concise and comprehensive format. Once the pharmacogenetic information is obtained and stored in the genetic database, software 124 may query the genetic database for patient's genetic information and the related pharmacogenetic information to determine patient genetic variations and other pertinent treatment or diagnosis data available for the patient.

Accordingly, the patient genetic information may be compared against the pharmacogenetic information for the purpose of processing the submitted medical request and to determine any conflicts (S240). If comparing the patient's genetic information with the pharmacogenetic information does not indicate a conflict or contraindication, then the medical request may be approved and the requested medical treatment or prescription may be administered to the patient or approved for the patient based on an understanding that the requested treatment is not adverse to one or more patient genetic attributes (S250). For example, an individual patient may be prescribed a medication for attention deficit disorder which is impacted by the gene COMT. If the patient's genetic profile indicates that he has a normal COMT gene activity, the medication may be administered to the patient with no alerts.

If a conflict is indicated (e.g., due to incompatibility between patient's genetic attributes and a medical treatment), then the request may be delayed or denied or an alert may be generated to notify a medical provider of the conflict (S260). For example, a warning may be generated that indicates potential adverse reactions, such as allergies, or potential adjustments to dosage for the particular patient. Other warnings may be generated to provide suggestions about alternate treatment regimens based on a history of successful or unsuccessful treatments (e.g., if a particular medical treatment or medication was not effective for the subject patient or patients in a similar genetic category or patients with the same or similar treatment history).

Figure 3A:
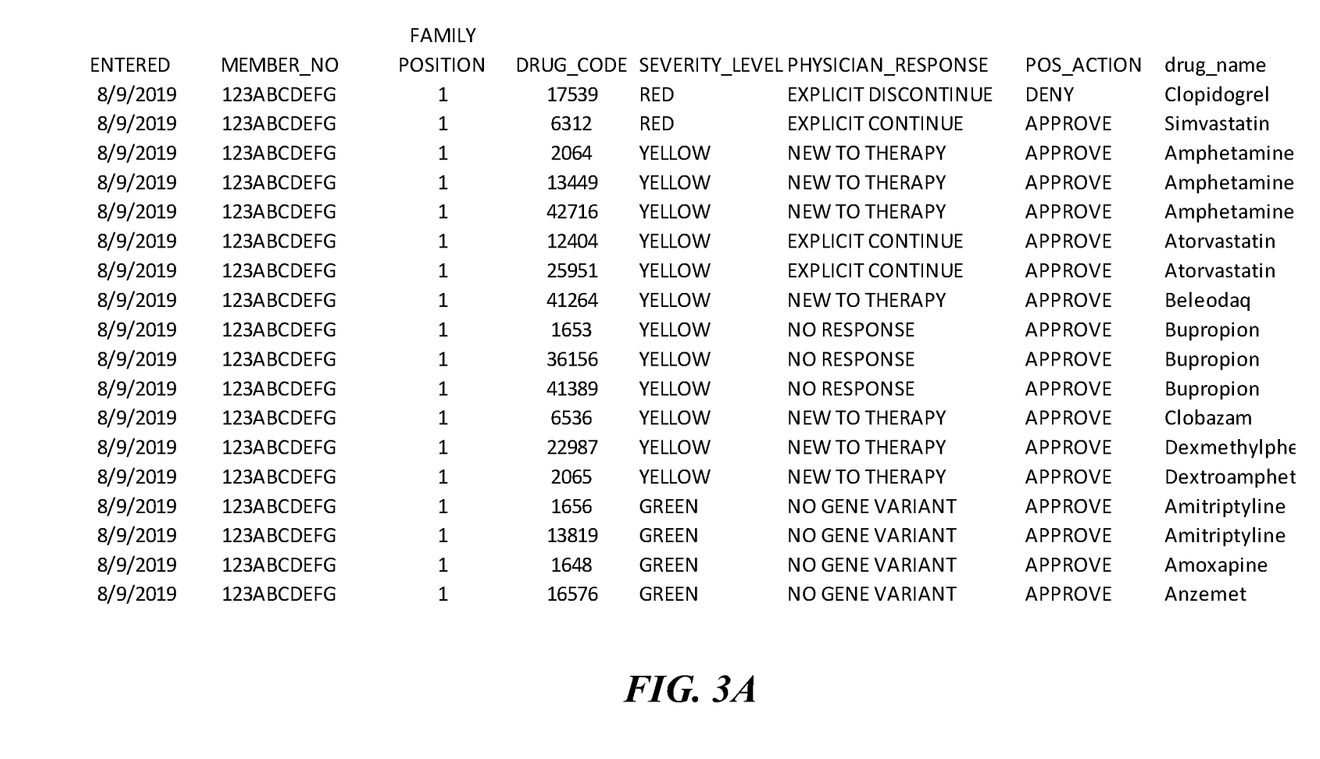
FIGS. 3A and 3B are example graphical user interfaces illustrating possible visual alerts and interactive user interface features for identifying contraindications or processing an order, in accordance with one or more embodiments, based on the personalization of the prescription adjudication system for individual patients.
Figure 3B:
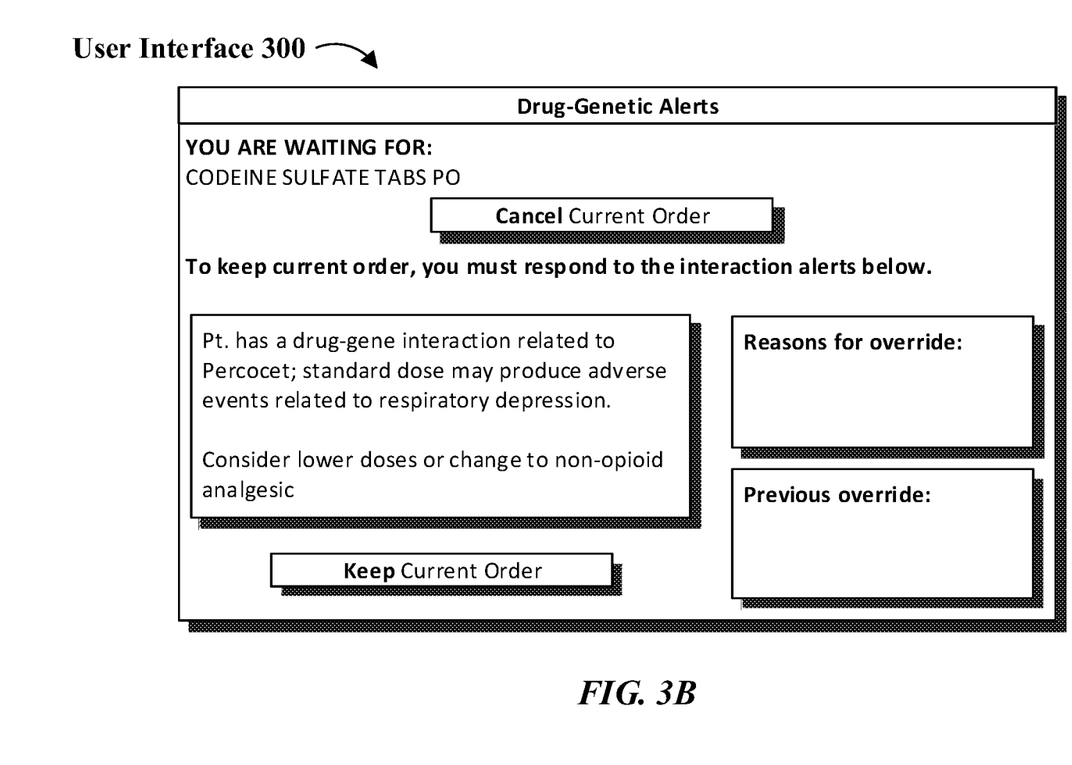

Referring to FIGS. 3A and 3B, in some implementations, the alert may be generated in real-time or near real-time, so that an end user is notified and is given the opportunity to withdraw the request and request the prescribing of an alternate medical treatment, prescription, test, etc. In certain embodiments, an authorized medical provider may be given the choice to override a denied request. In some aspects, one or more alternate choices (e.g., a list of compatible treatments, or generic prescription drug candidates) may be generated from which the ordering medical provider may choose. For example, the use of an opioid for pain relief may require a decrease in dose for those genetically determined to be rapid metabolizers. Alternatives presented to the prescriber may include a dose reduction or use of an alternative medication.

In certain implementations, if a conflict had been determined but the patient has a history of a prior claim for the same medication in the last six months, the requested medical treatment or prescription may be administer to the patient or approved for the patient based on an understanding that the requested treatment conflict has been communicated, acknowledged and accepted by the medical provider.

Referring back to FIGS. 3A and 3B, in certain embodiments, interactive user interfaces may be deployed to assist a user (e.g., a pharmacist, a medical provider, a patient, a technician, etc.) with the process of submitting a request through the operating environment 100. The graphical user interface may be implemented on computing system 110 and may include alert features that use a color scheme, for example, to identify any possible alerts associated with or adjustments that may need to be made to a medical request submitted for a particular patient based on any conflicts identified according to the patient's genetic information and the related pharmacogenetic information.

As shown in FIG. 3A, for example, a first color (e.g., green) may be used or displayed, in response to the user entering a designated medical treatment for the subject patient, if the patients genetic information does not conflict with the pharmacogenetic information. A second color (e.g., yellow) may be used or displayed, if the processing of the patient genetic information against the pharmacogenetic data indicates that some adjustment should be considered by the user. For example, a subscribing physician may want to consider adjusting the medication dosage in certain scenarios. A third color (e.g., red) may be used or displayed, if a certain risk is identified to the patient given the patient's genetic profile. In such example scenario, the physician may want to consider an alternate medication or treatment for the patient.

As shown in FIG. 3B, a user interface 300 may be provided to allow the user to interact with graphical user interface (GUI) menus, buttons or other GUI features to approve or cancel an order based on drug-genetic alerts and information displayed when an order is processed. In some embodiments, one or more user interfaces may be provided which characterize confidence in the suitability or reliability of a requested medical treatment for the subject patient. This interface may be implemented using artificial intelligence technology with a classification model that uses training data to determine the level of confidence in a certain medical request or treatment suggested for a patient by a medical provider.

In certain implementation, the confidence level may be provided in a variety of audiovisual ways. For example, a GUI display bar or a chart or a color scheme or an audio signal may be utilized to indicate the level of confidence. For instance, the length of an elongated bar, or a statistical graph of past successful trials, or a color code (see FIG. 3) may be used to indicate the measure of confidence (e.g., a longer bar indicates higher confidence, a shorter bar indicates lower confidence). Various other audiovisual alerts or indications that provide the same or similar functional features or results are within the scope of this disclosure, even if not disclosed in further detail herein.

In certain implementations, the feedback generated by the system may depend on a variety of personal attributes, such as whether the patient has been previously tested, diagnosis, risk factors, previously known results regarding success or failure of the ordered medication or treatment, etc. Such attributes are known factors in determining medications that best suit the patient for a variety of reasons. In the example of pharmacogenomics, the genetic information for an individual patient and the pharmacogenetic data may be used to determine a personalized formulary for a patient. The personalized formulary may include information about the patient's genetic results or makeup, latest scientific evidence for drug-to-gene-variant altered responses, the patient's diagnosis, or the patient's medication history and adherence rates. The personalization of medications is also possible based on other factors of diagnosis, health risks, etc. For example, an individual may be prescribed a nonsteroidal anti-inflammatory drug (NSAID). If the individual does not have a gene variation, no change in medication would be recommended. However, a drug-disease interaction may be reported if the individual has gastric disease.

As such, one or more embodiments of the disclosed subject matter may be utilized as a decision support system that assists a physician or healthcare provider with making a recommendation for patient treatment, where a patient's genetic profile and the pharmacogenetic test results are used to customize a personalized formulary for the patient. For example, incompatible medication may be removed in favor of alternatives for which a patient's genetic profile does not raise red flags as to compatibility and contraindications. In some aspects, medication or treatment costs or recommended dosages may also be adjusted for a patient, depending on a variety of factors or based on the subject patient's personalized formulary.

Accordingly, unlike currently available claim adjudication systems in which a physician prescribes and a pharmacy system adjudicates whether a prescription may be accepted or denied, the disclosed technology enables direct feedback to the physician. For example, the disclosed adjudication system herein, or the pharmacy, may communicate the need for a change directly to the physician at the time of care, instead of to the patient at the point of sale. In other examples, the physician may conduct a real time confirmation or validation at the point of prescribing a medication, using the disclosed claim adjudication technology, which is configured to customize the formulary for a patient based on pharmacogenetic results.

As provided herein, in accordance with one or more embodiments, in addition to medical claims adjudication, the disclosed technology may also allow for a care coordination capability to, for example, deny certain claims or visits to a healthcare provider, if a patient has not had her genetic profile analyzed. A patient could therefore be recommended for testing and an early clinical decision support system may be provided with dosing charts for a particular patient as integrated in electronic medical record systems or clinical decision support systems, so that prescribing providers can leverage pharmacogenetic recommendations for a patient at the time of care without delay and without having to rely on conjecture.

The advantages of the disclosed technology include improved instructions to a patient, dosage recommendations to a physician, and changes in medical recommendations to a physician based on a personalized longitudinal adjudication of medication (e.g., based on patient's personal profile including genetics and other personal data) with feedback to both doctors and patients at the time or during the course of treatment. The disclosed technology may be also configured to capture patient recorded outcomes, as well as cost of care, enabling feedback about certain outcomes, and providing the right medicine at the right dose with minimum of side effects for a patient based upon the patient's genetic profile. Advantageously, the disclosed technology may be also used to improve adherence to prescribed medication and further facilitate efficient communication among pharmacy or medical benefit manager, doctors, patients, and pharmacists, where the adjudication is continuous and not limited to a prescription being filled at the pharmacy.

Figure 4:
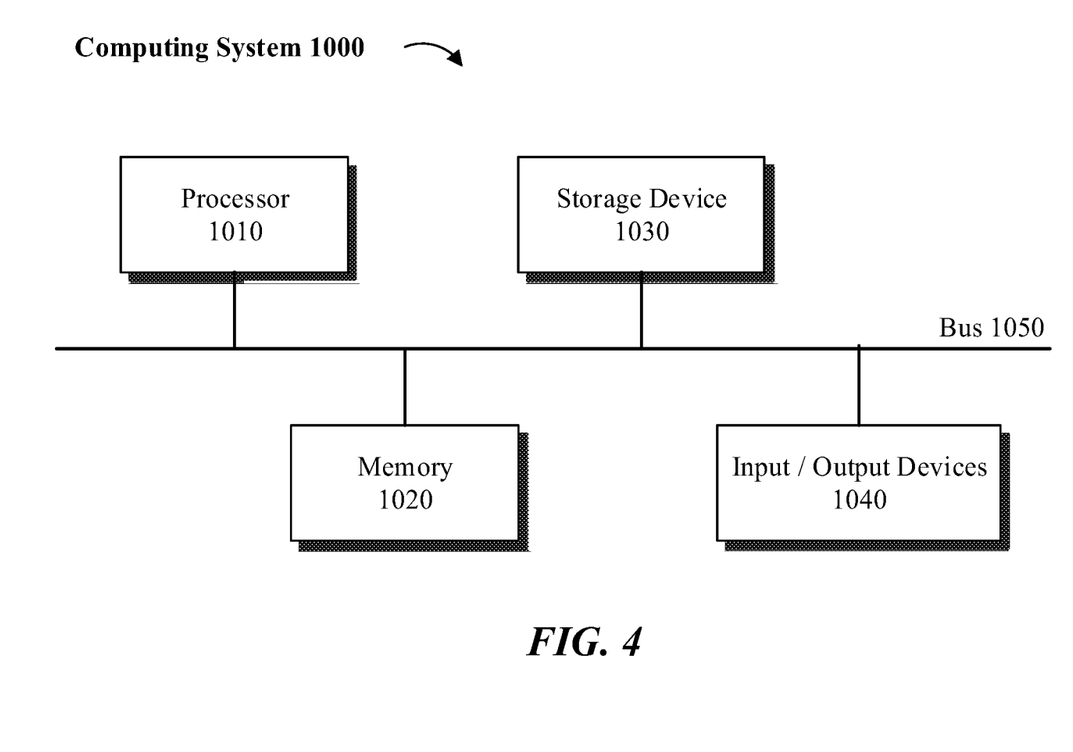
FIG. 4 is a block diagram of an example computing system that may be utilized to perform one or more computing operations or processes as consistent with one or more disclosed features.

Referring to FIG. 4, a block diagram illustrating a computing system 1000 consistent with one or more embodiments is provided. The computing system 1000 may be used to implement or support one or more platforms, infrastructures or computing devices or computing components that may be utilized, in example embodiments, to instantiate, implement, execute or embody the methodologies disclosed herein in a computing environment using, for example, one or more processors or controllers, as provided below.

As shown in FIG. 4, the computing system 1000 can include a processor 1010, a memory 1020, a storage device 1030, and input/output devices 1040. The processor 1010, the memory 1020, the storage device 1030, and the input/output devices 1040 can be interconnected via a system bus 1050. The processor 1010 is capable of processing instructions for execution within the computing system 1000. Such executed instructions can implement one or more components of, for example, a cloud platform. In some implementations of the current subject matter, the processor 1010 can be a single-threaded processor. Alternately, the processor 1010 can be a multi-threaded processor. The processor 1010 is capable of processing instructions stored in the memory 1020 and/or on the storage device 1030 to display graphical information for a user interface provided via the input/output device 1040.

The memory 1020 is a computer readable medium such as volatile or non-volatile that stores information within the computing system 1000. The memory 1020 can store data structures representing configuration object databases, for example. The storage device 1030 is capable of providing persistent storage for the computing system 1000. The storage device 1030 can be a floppy disk device, a hard disk device, an optical disk device, or a tape device, or other suitable persistent storage means. The input/output device 1040 provides input/output operations for the computing system 1000. In some implementations of the current subject matter, the input/output device 1040 includes a keyboard and/or pointing device. In various implementations, the input/output device 1040 includes a display unit for displaying graphical user interfaces.

According to some implementations of the current subject matter, the input/output device 1040 can provide input/output operations for a network device. For example, the input/output device 1040 can include Ethernet ports or other networking ports to communicate with one or more wired and/or wireless networks (e.g., a local area network (LAN), a wide area network (WAN), the Internet).

In some implementations of the current subject matter, the computing system 1000 can be used to execute various interactive computer software applications that can be used for organization, analysis and/or storage of data in various (e.g., tabular) format (e.g., Microsoft Excel®, and/or any other type of software). Alternatively, the computing system 1000 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 1040. The user interface can be generated and presented to a user by the computing system 1000 (e.g., on a computer screen monitor, etc.).

One or more aspects or features of the subject matter disclosed or claimed herein may be realized in digital electronic circuitry, integrated circuitry, specially designed application specific integrated circuits (ASICs), field programmable gate arrays (FPGAs) computer hardware, firmware, software, and/or combinations thereof. These various aspects or features may include implementation in one or more computer programs that may be executable and/or interpretable on a programmable system including at least one programmable processor, which may be special or general purpose, coupled to receive data and instructions from, and to transmit data and instructions to, a storage system, at least one input device, and at least one output device. The programmable system or computing system may include clients and servers. A client and server may be remote from each other and may interact through a communication network. The relationship of client and server arises by virtue of computer programs running on the respective computers and having a client-server relationship to each other.

These computer programs, which may also be referred to as programs, software, software applications, applications, components, or code, may include machine instructions for a programmable controller, processor, microprocessor or other computing or computerized architecture, and may be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium may store such machine instructions non-transitorily, such as for example as would a non-transient solid-state memory or a magnetic hard drive or any equivalent storage medium. The machine-readable medium may alternatively or additionally store such machine instructions in a transient manner, such as for example as would a processor cache or other random access memory associated with one or more physical processor cores.

To provide for interaction with a user, one or more aspects or features of the subject matter described herein may be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices may be used to provide for interaction with a user as well. For example, feedback provided to the user may be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive trackpads, voice recognition hardware and software, optical scanners, optical pointers, digital image capture devices and associated interpretation software, and the like.

Terminology

When a feature or element is herein referred to as being "on" another feature or element, it may be directly on the other feature or element or intervening features and/or elements may also be present. In contrast, when a feature or element is referred to as being "directly on" another feature or element, there may be no intervening features or elements present. It will also be understood that, when a feature or element is referred to as being "connected", "attached" or "coupled" to another feature or element, it may be directly connected, attached or coupled to the other feature or element or intervening features or elements may be present. In contrast, when a feature or element is referred to as being "directly connected", "directly attached" or "directly coupled" to another feature or element, there may be no intervening features or elements present.

Although described or shown with respect to one embodiment, the features and elements so described or shown may apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" may be intended to include the plural forms as well, unless the context clearly indicates otherwise. It will be further understood that the terms "comprises" and/or "comprising," when used in this specification, specify the presence of stated features, steps, operations, processes, functions, elements, and/or components, but do not preclude the presence or addition of one or more other features, steps, operations, processes, functions, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features due to the inverted state. Thus, the term "under" may encompass both an orientation of over and under, depending on the point of reference or orientation. The device may be otherwise oriented (rotated 90 degrees or at other orientations) and the spatially relative descriptors used herein interpreted accordingly. Similarly, the terms "upwardly", "downwardly", "vertical", "horizontal" and the like may be used herein for the purpose of explanation only unless specifically indicated otherwise.

Although the terms "first" and "second" may be used herein to describe various features/elements (including steps or processes), these features/elements should not be limited by these terms as an indication of the order of the features/elements or whether one is primary or more important than the other, unless the context indicates otherwise. These terms may be used to distinguish one feature/element from another feature/element. Thus, a first feature/element discussed could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, may represent endpoints or starting points, and ranges for any combination of the data points. For example, if a particular data point "10" and a particular data point "15" may be disclosed, it is understood that greater than, greater than or equal to, less than, less than or equal to, and equal to 10 and 15 may be considered disclosed as well as between 10 and 15. It is also understood that each unit between two particular units may be also disclosed. For example, if 10 and 15 may be disclosed, then 11, 12, 13, and 14 may be also disclosed.

Although various illustrative embodiments have been disclosed, any of a number of changes may be made to various embodiments without departing from the teachings herein. For example, the order in which various described method steps are performed may be changed or reconfigured in different or alternative embodiments, and in other embodiments one or more method steps may be skipped altogether. Optional or desirable features of various device and system embodiments may be included in some embodiments and not in others. Therefore, the foregoing description is provided primarily for the purpose of example and should not be interpreted to limit the scope of the claims and specific embodiments or particular details or features disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal.

The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the disclosed subject matter may be practiced. As mentioned, other embodiments may be utilized and derived therefrom, such that structural and logical substitutions and changes may be made without departing from the scope of this disclosure. Such embodiments of the disclosed subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve an intended, practical or disclosed purpose, whether explicitly stated or implied, may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The disclosed subject matter has been provided here with reference to one or more features or embodiments. Those skilled in the art will recognize and appreciate that, despite of the detailed nature of the example embodiments provided here, changes and modifications may be applied to said embodiments without limiting or departing from the generally intended scope. These and various other adaptations and combinations of the embodiments provided here are within the scope of the disclosed subject matter as defined by the disclosed elements and features and their full set of equivalents.

A portion of the disclosure of this patent document may contain material, which is subject to copyright protection. The owner has no objection to facsimile reproduction by any one of the patent documents or the patent disclosure, as it appears in the Patent and Trademark Office patent files or records, but reserves all copyrights whatsoever. Certain marks referenced herein may be common law or registered trademarks of the applicant, the assignee or third parties affiliated or unaffiliated with the applicant or the assignee. Use of these marks is for providing an enabling disclosure by way of example and shall not be construed to exclusively limit the scope of the disclosed subject matter to material associated with such marks.

What is claimed is:

1. A method comprising:
   generating, using one or more processors and in response to receiving a request to approve a medical request for administering clopidogrel to a patient, a first database query to obtain at least one of a gene variant of the patient or a genetic disposition of a population of persons to whom the patient is genetically related;
   generating, using the one or more processors, a second database query to obtain blood clot formation risks of the patient from a database of personal clinical variable information;
   comparing, using the one or more processors, at least one of the gene variant of the patient or the genetic disposition of the population of persons against a database of pharmacogenetic information in view of the medical request for administering clopidogrel to the patient;
   comparing, using the one or more processors, the blood clot formation risks of the patient against the database of personal clinical variable information in view of the medical request for administering clopidogrel to the patient, the database of personal clinical variable information including blood clot formation risks of persons having a stent in a cardiac vessel; and
   administrating clopidogrel to the patient in response to determining that clopidogrel is compatible with genetic attributes of the patient determined based on the comparing the at least one of the gene variant or the genetic disposition of the population of persons against the database of pharmacogenetic information and based on the comparing of the blood clot formation risks against the database of personal clinical variable information.

2. The method of claim 1, wherein the request is processed by a claim processing system with access to a database of claims history for the patient.

3. The method of claim 1, wherein the at least one of gene variants or the genetic disposition of the population of persons of the patient is provided by a third party vendor.

4. The method of claim 1, wherein the gene variant comprises at least one of a single nucleotide polymorphisms (SNP) or a deletion.

5. The method of claim 4, wherein the SNP is at least one of a missense mutation or a nonsense mutation.

6. The method of claim 1, wherein the genetic disposition of the population of persons to whom the patient is genetically related comprises data about at least one of renal function, liver function, nationality, ethnicity, or race.

7. The method of claim 1, wherein the database of personal clinical variable information comprises information about at least one of:
   disease diagnosis including comparative information of drug-disease interactions,
   body surface area including comparative information of drug doses,
   body mass including comparative information of drug doses, or
   drugs impacted by smoking induced enzyme production.

8. The method of claim 1, wherein the database of personal clinical variable information comprises information about publicly available demographic data associated with at least one of general transportation costs, food costs, or patient-provided demographic data to compare to affordability of prescribed medical treatment.

9. The method of claim 1, wherein the gene variant of the patient comprises an insertion.

10. The method of claim 1, wherein the gene variant of the patient comprises at least one of a duplication, a frameshift mutation, or a repeat expansion.

11. The method of claim 1, wherein the database of pharmacogenetic information comprises comparative information indicating the clopidogrel may be ineffective based on the at least one of gene variants or the genetic disposition of the population of persons.

12. The method of claim 1, wherein the database of pharmacogenetic information comprises comparative information indicating the clopidogrel may cause an adverse reaction based on the at least one of gene variants or the genetic disposition of the population of persons.

13. The method of claim 1, wherein the database of pharmacogenetic information is linked to a database of alternative solutions for the clopidogrel requested.

14. The method of claim 1, wherein the response comprises at least one of: a warning, an alternative treatment solution, a denial of the request, an approval of the request, an alternative dosage associated with a prescribed medication as a part of the request, a suggestion for suggesting administration of a genetic test to the patient.

15. The method of claim 2, wherein a user of the claim processing system comprises at least one of: a pharmacist, the patient, a prescribing physician, a physician assistant, or an insurance representative.

16. The method of claim 1, further comprising continuously updating at least one of the database of pharmacogenetic information and the database of genetic information, wherein the updating comprises adding new data to the database of pharmacogenetic information based on domestic or international genetic research.

* * * * *